United States Patent [19]

Baldwin et al.

[11] Patent Number: 4,616,017

[45] Date of Patent: Oct. 7, 1986

[54] AMINOHYDROXYPROPOXY SUBSTITUTED ARYL COMPOUNDS

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 617,297

[22] Filed: Jun. 4, 1984

[51] Int. Cl.[4] .................. C07D 401/04; C07D 211/00; A61K 31/495; A61K 31/435
[52] U.S. Cl. ..................................... 514/252; 544/121; 544/129; 544/360; 544/366; 544/370; 544/377; 544/379; 544/391; 544/394; 546/184; 546/192; 546/193; 546/197; 546/198; 546/199; 546/214; 546/225; 546/245; 514/255; 514/315; 514/317; 514/318; 514/321; 514/322; 514/326; 514/330
[58] Field of Search ............... 544/360, 391, 394, 370, 544/366, 377, 121, 129; 546/192, 193, 245, 184; 424/250, 267

[56] References Cited

U.S. PATENT DOCUMENTS

| | | | |
|---|---|---|---|
| 3,941,789 | 3/1976 | Renth | 544/370 |
| 3,959,283 | 5/1976 | Lafon | 544/370 |
| 3,965,106 | 6/1976 | Maryama et al. | 544/391 |
| 4,134,983 | 1/1979 | Baldwin | 544/370 |
| 4,255,575 | 3/1981 | Grisar et al. | 544/360 |
| 4,440,774 | 4/1984 | Baldwin | 544/370 |
| 4,469,693 | 9/1984 | Bagli et al. | 544/370 |
| 4,485,258 | 11/1984 | Kikumoto et al. | 544/391 |

FOREIGN PATENT DOCUMENTS

| | | | |
|---|---|---|---|
| 743494 | 6/1970 | Belgium | 544/394 |
| 1317479 | 5/1973 | United Kingdom | 544/394 |

*Primary Examiner*—George F. Lesmes
*Assistant Examiner*—S. A. Gibson
*Attorney, Agent, or Firm*—Alice O. Robertson; William H. Nicholson; Michael C. Sudol

[57] ABSTRACT

Novel tertiary aminohydroxypropoxy substituted aryl compounds exhibit $\alpha_1$-adrenoceptor and serotonin antagonism and are also useful as antihypertensive agents.

6 Claims, No Drawings

AMINOHYDROXYPROPOXY SUBSTITUTED ARYL COMPOUNDS

SUMMARY OF THE INVENTION

This invention is concerned with a novel compound of structural formula:

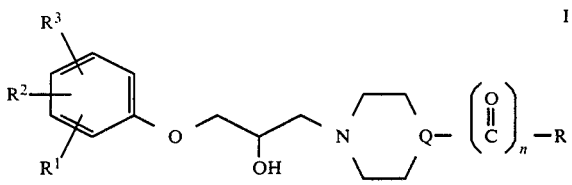

wherein Q is >N— or >CH— or a pharmaceutically acceptable salt thereof wherein n, R, $R^1$, $R^2$, and $R^3$ are as defined below, which have $\alpha_1$-adrenoceptor and serotonin blocking properties and hence useful in the treatment of hypertension and certain related conditions.

The invention is also concerned with processes for the preparation of the novel compounds; pharmaceutical formulations comprising one or more of the novel compounds as active ingredient; and a method of treating hypertension, gastrointestinal ulcers, bronchial spasm, varices, hemorrhoids and related congestive disorders, and elevated intraocular pressure.

BACKGROUND OF THE INVENTION

There are various classes of antihypertensive drugs including the diuretics such as hydrochlorothiazide, angiotensin converting enzyme inhibitors such as enalapril, β-blockers such as timolol, $\alpha_1$-blockers such as prazosin, and mixed $\beta/\alpha_1$-adrenergic receptor antagonists such as labetolol.

Now, with the present invention there is provided a class of compounds that structurally resemble the well known β-blockers, with the aryloxypropanolamine skeleton, but which are almost devoid of β-blocking activity and demonstrate $\alpha_1$-adrenergic receptor antagonism and a component of serotonin antagonism.

DETAILED DESCRIPTION OF THE INVENTION

The novel compounds of this invention have structural formula I:

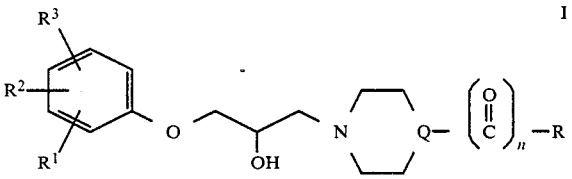

or a pharmaceutically acceptable salt thereof wherein:
$R^1$ is:
 (1) hydrogen,
 (2) hydroxy, or
 (3) hydroxymethyl;
$R^2$ and $R^3$ are independently:
 (1) hydrogen,
 (2) halo such as chloro, bromo or fluoro,
 (3) hydroxy,
 (4) amino,
 (5) di($C_{1-5}$alkyl)amino,
 (6) mono($C_{1-5}$alkyl)amino,
 (7) nitro,
 (8) cyano,
 (9) $C_{1-6}$alkyl,
 (10) $C_{3-8}$cycloalkyl,
 (11) $C_{2-5}$alkenyl,
 (12) $C_{1-4}$alkoxy,
 (13) $C_{1-4}$alkylthio
 (14) $C_{2-5}$alkenyloxy,
 (15) $C_{1-5}$alkanoyl, such as formyl, pentanoyl or the like.
Q is >N— or >CH—;
n is 0 or 1; and
R is
 (1) $C_{1-4}$alkyl, substituted with:
  (a) carbocycle or heterocycle of 5 to 10 nuclear atoms, 1 or 2 rings, and up to 3 heteroatoms selected from O, N and S such as phenyl, naphthyl,

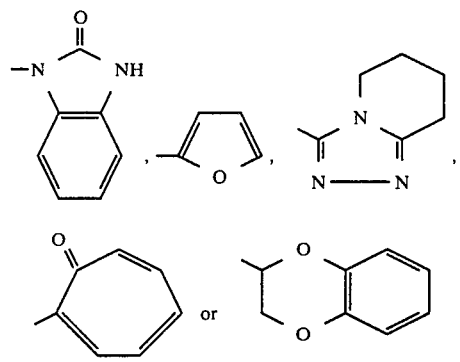

and either unsubstituted or substituted with
 (i) $C_{1-3}$alkyl,
 (ii) halo such as chloro, bromo or fluoro,
 (iii) cyano, or
 (iv) $C_{1-3}$alkoxy; or
 (2) a carbocycle or heterocycle as previously defined.

Preferred are those compounds of Formula I, wherein one of $R^1$ and $R^2$ are hydrogen, $R^3$ is cyano: and R is phenyl, methoxyphenyl, halophenyl, or halopyridyl, especially 3- or 5-fluoro-2-pyridyl.

The novel compounds of this invention include all the optical isomer forms as pure enantiomers or as mixtures containing the optical isomers such as racemic mixtures and compounds.

The compounds of the present invention also include the non-toxic pharmaceutically acceptable acid addition and quaternary ammonium salts. The acid addition salts are prepared by treating the compounds with an appropriate amount of a suitable organic or inorganic acid. Examples of useful organic acids are carboxylic acids such as maleic acid, tartaric acid, acetic acid, pamoic acid, oxalic acid, propionic acid, salicylic acid, succinic acid, citric acid, malic acid, isethionic acid, and the like. Useful inorganic acids are hydrohalo acids such as hydrochoric, hydrobromic, hydriodic, sulfuric, phosphoric acid, or the like.

The novel process of this invention is illustrated as follows:

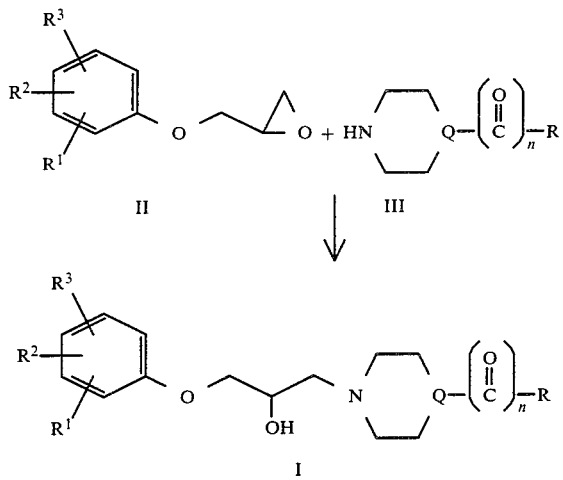

wherein Q and n are as defined above.

An epoxide II is reacted with an amine of the type III in a suitable solvent such as methanol, ethanol, isopropanol, methylene chloride, THF or the like, at 0° C. to the reflux temperature of the solvent for about 1–48 hours, preferably in isopropanol at about 70° C. for 24 hours, to yield I. The epoxide moiety of II may be prepared in chiral (R or S) form and if utilized in the above reaction would provide compound I in the (R)- or (S)-conformation, respectively.

The compounds of the present invention are active (1) as antihypertensives, i.e., they have an immediate blood pressure lowering effect in hypertensive animals; (2) as $\alpha_1$-adrenergic receptor antagonists, and useful in the treatment of elevated intraocular pressure; and (3) as serotonin antagonists; i.e., they reduce and minimize lesions caused by excessive serotonin release and block serotonin-induced contractions of bronchial tissues and of blood vessels, arteries and veins. Thus, the compounds of the present invention are useful to treat gastrointestinal ulcers, bronchial spasms, varices, hemorrhoids and similar diseases caused by congestion.

The antihypertensive effect is determined by administering (orally or intraperitoneally) compound to spontaneously hypertensive (SH) rats and measuring the effect on the blood pressure. A representative compound of this invention was found to lower the SH rats' blood pressure.

The $\alpha_1$-antagonist activity ($\alpha_1$-blockade) of the present compounds was determined by measuring the ability of representative compounds to block methoxamine induced contraction using cat vas deferens tissue. Several compounds were also shown to bind specifically to the serotonin-$S_2$-receptor using $^3$[H]spiperone as ligand and to the $\alpha_1$-receptor using $^3$[H]prazosin as ligand. Representative examples of the novel compounds demonstrated $\alpha_1$-blockade, $\alpha_1$- and $S_2$-binding in addition to having the aforesaid antihypertensive effect.

The ability of the compounds of the present invention to reduce blood pressure in the SH rat indicates that the compounds and their salts may be useful in treating essential hypertension in humans.

For use as antihypertensives, serotonin, and/or $\alpha_1$-blocking agents, the present compounds can be administered orally, topically, or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsified; (c) transdermal application; or (d) in an ophthalmic formulation for topical ocular administration for the treatment of elevated intraocular pressure such as glaucoma. The ratio of active compound to compounding ingredients; i.e., carrier, diluent, etc., will vary as the dosage form requires. Whatever dosage form is used, the amount of compound of the present invention administered should be sufficient to effect (a) a reduction in blood pressure of the patient suffering from hypertension and/or (b) desirable level of $\alpha_1$-adrenoceptor blockade in the patient, and/or (c) inhibit serotonin release. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

Combination of the novel compounds of this invention with other active medicinal agents such as $\beta$-blockers, diuretics, antihypertensives and other serotonin antagonists is contemplated by this invention.

Following are examples illustrating representative pharmaceutical formulations containing compounds of the present invention. Conventional techniques are used to prepare these formulations.

TABLET FORMULATION

| INGREDIENT | AMOUNT (Mg.) |
|---|---|
| 1-[3-(4-Chlorophenoxy)-2-hydroxypropyl]-4-(3-fluoro-2-pyridyl)piperazine | 40.0 |
| calcium phosphate | 120.0 |
| lactose | 50.0 |
| starch | 23.5 |
| magnesium stearate | 1.5 |

CAPSULE FORMULATION

| INGREDIENT | AMOUNT (Mg.) |
|---|---|
| 1-[3-(2-Cyanophenoxy)-2-hydroxypropyl]-4-(3-fluoro-2-pyridyl)piperazine | 250 |
| lactose, U.S.P. | 93 |
| talc | 7 |

INJECTABLE SOLUTION

| INGREDIENT | AMOUNT (Mg.) |
|---|---|
| 2-[[3-[4-Fluorobenzoyl)-piperidine-1-yl]-2-hydroxy]propoxy]benzonitrile | 5 |
| sodium chloride | 9 |
| distilled water, q.s. 1.0 ml. | |

LIQUID SUSPENSION

| INGREDIENT | AMOUNT (Mg.) |
| --- | --- |
| 2-[[3-[4-Fluorobenzoyl)piperidine-1-yl]-2-hydroxy]propoxy]benzonitrile | 5.0 |
| Veegum H.V. | 3.0 |
| methyl paraben | 1.0 |
| kaolin | 10.0 |
| glycerin | 250.0 |
| water, q.s. 1 liter | |

The following examples illustrate preparation of representative compounds of the present invention. Unless otherwise indicated, all parts and percentages are by weight, all temperatures are in degrees Celsius, and all analyses were computed to within 0.4%.

EXAMPLE 1

1-[3-(4-Chlorophenoxy)-2-hydroxypropyl]-4-(3-fluoro-2-pyridyl)piperazine

To 1-(3-fluoro-2-pyridyl)piperazine (453 mg, 2.5 mmol) in 5 ml of isopropanol stirred under nitrogen at 70° C. was added 4-chlorophenoxy-2,3-epoxypropane (476 mg, 2.5 mmol) portionwise and the solution stirred at 70° C. for 3 hours The solution was concentrated in vacuo and the residual oil chromatographed on silica gel eluting with 5% methanol-chloroform to yield 740 mg (81%) of 1-[3-(4-chlorophenoxy)-2-hydroxypropyl]-4-(3-fluoro-2-pyridyl]piperazine; m.p. 73°-76° C. Analysis satisfactory for $C_{18}H_{21}ClFN_3O_2$.

EXAMPLE 2

1-[3-(2-Cyanophenoxy)-2-hydroxypropyl]-4-(3-fluoro-2-pyridyl)piperazine

To a solution of 1-(3-fluoro-2-pyridyl)piperazine (453 mg, 2.5 mmol) in 5 ml of isopropanol stirred at 70° C. under nitrogen was added portionwise 2-cyanophenoxy-2,3-epoxypropane (438 mg, 2.5 mmol) and the mixture stirred for 2½ hours at 70° C. The solvent was removed in vacuo at room temperature and the residual oil was chromatographed on silica gel eluting with 5% methanol-chloroform. The product was obtained as a colorless oil which slowly solidified upon trituration in hexane to yield 0.66 g of 1-[3-(2-cyanophenoxy)-2-hydroxypropyl]-4-(3-fluoro-2-pyridyl)piperazine; m.p. 68°-70° C. Analysis satisfactory for $C_{19}H_{21}FN_4O_2$.

EXAMPLE 3

2-[[3-[4-Fluorobenzoyl)piperidine-1-yl]-2-hydroxyl]propoxy]benzonitrile

2-Cyanophenoxy-2,3-epoxypropane (1.23 g, 7 mmol) and 4-(4-fluorobenzoyl)piperidine (1.45 g, 7 mmol) (prepared from the HCl salt just prior to use) were heated overnight in isopropanol (20 ml) at 40° C. The white product was separated by filtration, washed with isopropanol (20 ml), ether and dried in vacuo to yield 2.1 g (78%) of 2-[[3-[4-fluorobenzoyl)piperidine-1-yl]-2-hydroxy]propoxy]benzonitrile; m.p. 144°-145° C. Analysis satisfactory for $C_{22}H_{23}N_2O_3F_2$.

Employing the procedures substantially as described in Examples 1 through 3, but using as starting materials, the cyclic amines described in Table I, there are produced the tertiary aminohydroxypropoxy substituted aryl compounds also described in Table I in accordance with the following reaction scheme:

TABLE I

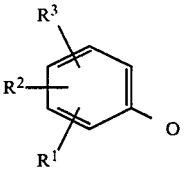

| R¹ | R² | R³ | Q | n | R |
| --- | --- | --- | --- | --- | --- |
| 2-Cl | 4-CH₃ | 5-OCH₃ | 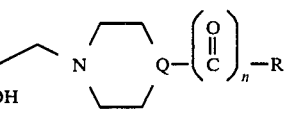 | 0 | 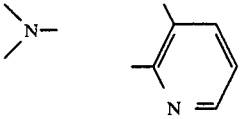 |
| 2-CN | H | H | 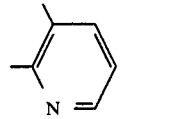 | 0 | 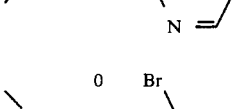 |
| 3-Cl | 4-Cl | H | 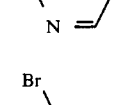 | 0 | |

TABLE I-continued $$\text{R}^3\text{-}\text{R}^2\text{-}\text{R}^1\text{-C}_6\text{H}_3\text{-O-CH}_2\text{-CH(OH)-CH}_2\text{-N(piperazine)-Q-}(\overset{O}{\underset{\|}{C}})_n\text{-R}$$

| R¹ | R² | R³ | Q | n | R |
|---|---|---|---|---|---|
| 3-F | H | H | >N— | 0 | 3-cyano-pyrazin-2-yl |
| 3-N(CH₃)₂ | H | H | >N— | 0 | 4-methoxy-2-methylpyrimidin-?-yl |
| 3-Br | 4-OCH₃ | H | >N— | 0 | 3,4-dimethylpyridazin-?-yl |
| 3-$\overset{O}{\underset{\|}{C}}$CH₂CH₂CH₃ | H | H | >N— | 0 | 2,3-dimethylpyridin-?-yl |
| 4-CF₃ | H | H | >N— | 0 | 3-cyano-2-methylpyridin-?-yl |
| 3-OH | 4-CH₃ | | >N— | 0 | 5-bromo-2-methylpyridin-?-yl |
| 2-CN | H | H | >CH— | 0 | 2-oxo-2,3-dihydro-1H-benzimidazol-1-yl |
| 2-CN | H | H | >N— | 1 | furan-2-yl |
| 2-CN | H | H | >N— | 0 | —CH₂CH₂—(6,7,8,9-tetrahydro-1,2,4-triazolo-pyridine-type) |

TABLE I-continued

Structure: R³, R², R¹ substituted phenyl—O—CH₂—CH(OH)—CH₂—N(piperazine)—Q—(C=O)ₙ—R

| R¹ | R² | R³ | Q | n | R |
|---|---|---|---|---|---|
| 2-CN | H | H | >N— | 0 | 2-oxocyclohepta-3,5,7-trien-1-yl |
| 2-CN | H | H | >N— | 0 | 1,4-benzodioxan-2-yl |
| 3-C(O)NH-CH₃ | H | H | >N— | 0 | 3-cyanopyridin-2-yl |
| H | H | 6-CN | >CH— | 1 | 4-fluorophenyl |
| 3-Cl | 4-Cl | H | >CH— | 1 | 2-fluorophenyl |
| 3-OCH₂CH₃ | 4-Br | H | >CH— | 1 | 2-chlorophenyl |
| 4-C(O)CH₂CH₃ | 5-F | H | >CH— | 1 | 3-bromophenyl |
| 3-N(morpholino) | H | H | >CH— | 1 | 2-methoxyphenyl |
| 4-OH | H | H | >CH— | 1 | 4-ethylphenyl |
| 3-Cl | 4-OH | H | >CH— | 1 | 2,3-dimethoxyphenyl |

TABLE I-continued

| R¹ | R² | R³ | Q | n | R |
|---|---|---|---|---|---|
| 3-C(O)NH₂ | H | H | >CH— | 1 | 2-Cl, 4-OH phenyl (2-chloro-4-hydroxyphenyl) |
| 3-C(O)NHCH₃ | H | H | >CH— | 1 | 2-CH₃, 4-OH phenyl |
| 3-C(O)N(CH₂CH₃)₂ | H | H | >CH— | 1 | 2-OCH₃, 4-OH phenyl |
| 4-CF₃ | H | H | >CH— | 1 | 2-OCH₃, 4-F phenyl |
| 3-CF₃ | 4-CH₃ | H | >CH— | 1 | 2-OCH₃, 4-CH₃ phenyl |

What is claimed is:

1. A compound of structural formula:

or a pharmaceutically acceptable salt thereof wherein:

R¹ is
 (1) hydrogen,
 (2) hydroxy, or
 (3) hydroxymethyl;

R² is
 (1) hydrogen,
 (2) halo,
 (3) hydroxy,
 (4) nitro,
 (5) cyano,
 (6) $C_{1-6}$alkyl,
 (7) $C_{3-8}$cycloalkyl,
 (8) $C_{2-5}$alkenyl,
 (9) $C_{1-4}$alkoxy,
 (10) $C_{1-4}$alkylthio,
 (11) $C_{2₁-5}$alkenyloxy, or
 (12) $C_{1-5}$alkanoyl; and R³ is
 (1) hydrogen or
 (2) cyano;

Q is >N— or >CH—;

n is 0 or 1; and

R is
 (1) phenyl,
 (2) methoxyphenyl
 (3) halophenyl, or
 (4) halopyridyl;

provided that one of R¹ and R² is hydrogen.

2. The compound of claim 1 which is 1-[3-(4-chlorophenoxy)-2-hydroxypropyl]-4-(3-fluoro-2-pyridyl)piperazine;

1-[3-(2-cyanophenoxy)-2-hydroxyproyl]-4-(3-fluoro-2-pyridyl)piperazine;

2-[[3-[4-fluorobenzoyl)piperidine-1-yl]-2-hydroxy]-propoxy]benzonitrile;

or a pharmaceutically acceptable salt thereof.

3. A pharmaceutical composition useful as α₁-adrenergic receptor antagonists, or serotonin antagonists comprising a pharmaceutically acceptable carrier and a therapeutically effective amount of a compound as defined in claim 1 or a pharmaceutically acceptable salt thereof.

4. The pharmaceutical composition of claim 3 wherein the compound is as defined in claim 2 or a pharmaceutically acceptable salt thereof.

5. A method of antagonizing $\alpha_1$-adrenergic receptors and serotonin release which comprises the administration to a patient in need of such treatment of an effective amount of the compound of claim 1 or a pharmaceutically acceptable salt thereof.

6. The method of claim 5 wherein the compound is as defined in claim 3 or a pharmaceutically acceptable salt thereof.

* * * * *